United States Patent [19]

Linkies et al.

[11] Patent Number: 4,618,455
[45] Date of Patent: Oct. 21, 1986

[54] PROCESS FOR PREPARING CRYSTALLINE SALTS OF ACETOACETAMIDE-N-SULFOFLUORIDE

[75] Inventors: Adolf Linkies, Frankfurt am Main; Dieter Reuschling, Butzbach, both of Fed. Rep. of Germany

[73] Assignee: Hoechst Aktiengesellschaft, Frankfurt am Main, Fed. Rep. of Germany

[21] Appl. No.: 713,466

[22] Filed: Mar. 19, 1985

[30] Foreign Application Priority Data

Mar. 21, 1984 [DE] Fed. Rep. of Germany ....... 3410233

[51] Int. Cl.$^4$ ........................................... C07C 143/70
[52] U.S. Cl. .................................................. 260/543 F
[58] Field of Search ...................................... 260/543 F

[56] References Cited

U.S. PATENT DOCUMENTS 3,689,486  9/1972  Clauss et al. ..................... 260/543 F
4,052,453 10/1977  Pietsch et al. ................... 260/543 F

FOREIGN PATENT DOCUMENTS 2453063  5/1976  Fed. Rep. of Germany ... 260/543 F

Primary Examiner—Natalie Trousof
Assistant Examiner—L. Hendriksen
Attorney, Agent, or Firm—Curtis, Morris & Safford

[57] ABSTRACT

Crystalline salts of acetoacetamide-N-sulfofluoride are prepared by reacting amidosulfofluoride $H_2NSO_2F$ with diketene in the presence of inorganic bases, preferably alkali metal carbonates and/or hydrogencarbonates, in particular potassium carbonate, in an inert organic solvent.

The salts can be further processed with further base, for example with methanolic KOH, into salts of 6-methyl-3,4-dihydro-1,2,3-oxathiazin-4-one-2,2-dioxide; the potassium salt, in particular, is important for use as a sweetener ("Acesulfame").

7 Claims, No Drawings

PROCESS FOR PREPARING CRYSTALLINE SALTS OF ACETOACETAMIDE-N-SULFOFLUORIDE

Acetoacetamide-N-sulfofluoride is the compound of the formula $$CH_3-CO-CH_2-CONHSO_2F.$$

Owing to the acidic hydrogen on the nitrogen atom, the compound is capable of forming salts (with bases). The salts, for example the triethylammonium salt, are in the main intermediates, in particular for preparing the nontoxic salts of 6-methyl-3,4-dihydro-1,2,3-oxathiazin-4-one-2,2-dioxide, which, owing to their, in some cases, pronounced sweet taste, can be used as sweeteners in foods. Of the non-toxic salts of 6-methyl-3,4-dihydro-1,2,3-oxathiazin-4-one-2,2-dioxide, the potassium salt ("Acesulfame K" or just "Acesulfame") is of particular importance. The sweetener Acesulfame is obtained for example from the triethylammonium salt of acetoacetamide-N-sulfofluoride by reaction with 2 equivalents of a potassium base, for example KOH, preferably in methanolic or aqueous solution:

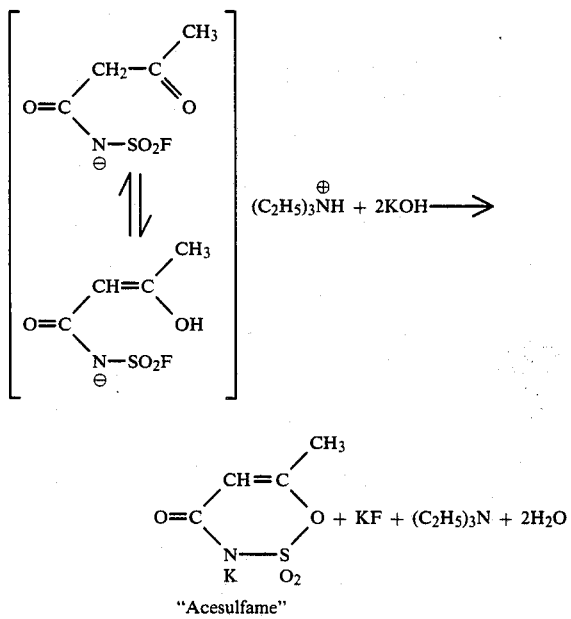

"Acesulfame"

It has been disclosed, in German Offenlegungsschrift No. 2 453,063, to react the salts of acetoacetamide-N-sulfofluoride with organic nitrogen bases by reacting amidosulfofluoride $H_2NSO_2F$ with an at least approximately equimolar amount of diketene at temperatures between about $-30°$ and $+100°$ C., preferably between about $-20°$ and $+50°$ C., in particular between about $-10°$ and $+30°$ C., in the presence of at least one gram equivalent of an organic nitrogen base per mol of amidosulfofluoride and in the absence or presence of an inert organic solvent. If, for example, triethylamine is used as the organic nitrogen base the reaction proceeds as shown in the following diagram:

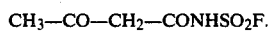

The thereby obtainable salts of acetoacetamide-N-sulfofluoride with organic nitrogen bases are usually obtained in the form of non-crystalline brownish compounds of oily consistency and only in exceptional cases in solid, crystalline form. Of the 12 illustrative embodiments given in German Offenlegungsschrift No. 2,453,063, only in a single case (Example 12) is the product (the tetramethylethylenediamine salt of acetoacetamide-N-sulfofluoride) reported as solid and crystalline.

Since the formation of non-crystalline oily products virtually always constitutes a certain disadvantage, it is the object of the present invention to prepare salts of acetoacetamide-N-sulfofluoride which are, without exception, crystalline.

This object is achieved according to the invention in the main by replacing the organic nitrogen bases in the process of German Offenlegungsschrift No. 2,453,063 by inorganic bases.

The invention accordingly provides a process for preparing crystalline salts of acetoacetamide-N-sulfofluoride by reacting amidosulfofluoride with diketene in the presence of bases in an inert organic solvent; in the process, the bases used are inorganic bases.

Preferred inorganic bases are carbonates and hydrogencarbonates of the alkali metals (lithium, sodium, potassium, rubidium and cesium), particular preference being given to potassium carbonate and potassium hydrogen carbonate, especially potassium carbonate. The amount of inorganic base to be used is advantageously at least about 1 gram equivalent per mol of amidosulfofluoride. However, preferably the bases are used in excess up to about 20%, in particular only up to about 10%. It is generally advisable and sufficient to use an amount of inorganic base such that at the end of the reaction the reaction mixture according to the invention is at at least pH 7, as measured with moist pH indicator paper.

The salts of acetoacetamide-N-sulfofluoride produced in the process, in yields which are in all cases between about 85 and 95% of theory, based on amidosulfofluoride, are without exception crystalline solids. A particular advantage over the process of said German Offenlegungsschrift No. 2,453,063 also resides in the use of (compared with the organic nitrogen bases) simpler and less costly inorganic bases. Finally, the preparation of, for example, the sweetener Acesulfame from amidosulfofluoride by way of the process according to the invention requires per mol of amidosulfofluoride a total of about 2 (or only little more than 2) gram equivalents of a potassium base, while the preparation by way of the process of German Offenlegungsschrift No. 2,453,063 requires at least one gram equivalent of an organic nitrogen base and at least about 2 equivalents of a potassium base, and the organic nitrogen base has to be recovered in an additional process step.

The fact that solid crystalline salts of acetamido-N-sulfofluoride are obtained in high yields at the end of a smooth reaction is very surprising because normally the salts of organic nitrogen bases (ammonium salts) and inorganic salts—in particular alkali metal salts—with the same anionic salt component in each case are of the same physical consistency. Another reason why the smooth and fast course of the reaction was unexpected as well is that the inorganic bases used according to the invention are sparingly soluble in the organic reaction medium (heterogenous reaction!).

The reaction according to the invention proceeds, analogously to the reaction described in German Offenlegungsschrift No. 2,453,063, according to the following diagram (with potassium carbonate as the inorganic base):

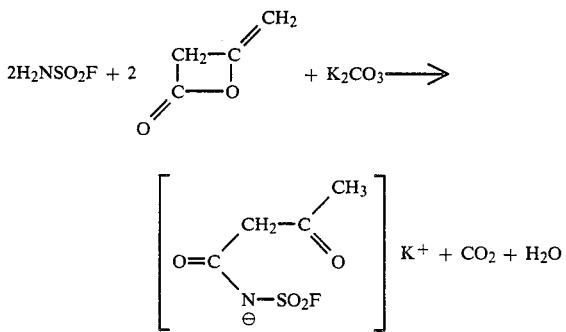

The amount of diketene used should be at least substantially equimolar relative to the reactant amidosulfofluoride. It is preferred to use the diketene in an excess of up to about 30 mol %, in particular an excess between about 10 and 20 mol %. Excesses greater than about 30 mol % are possible, but do not yield any further benefit.

The inert organic solvent can be virtually any organic solvent which does not react in an undesirable manner with the starting and end materials (including the inorganic bases). The following organic solvents are mentioned is examples of what can be used:

Low aliphatic ketones, preferably of 3 to 6 carbon atoms, such as, for example, acetone, methyl ethyl ketone and so on; aliphatic ethers, preferably cyclic aliphatic ethers of 4 to 5 carbon atoms, such as, for example, tetrahydrofuran, dioxane and so on; N-alkyl-substituted amides of low aliphatic carboxylic acids, preferably those of up to a total of 7 carbon atoms, such as, for example, dimethylformamide; aliphatic sulfoxides, preferably dimethyl sulfoxide and aliphatic sulfones, preferably sulfolane.

Of the solvents listed in the preceding paragraph, particular preference - on grounds of reaction control - is given to those whose boiling points are within the range of the desired reaction temperature; they are chiefly in this instance acetone, acetonitrile and dimethylformamide, especially acetone.

The solvents can be used not only alone but also mixed.

The mixing ratio of reactive starting materials to solvent can vary within wide limits. The ratio by weight is generally of the order of 1:(2-20).

The reaction temperature is practically within the same range as that of the process claimed in German Offenlegungsschrift No. 2,453,063; the temperatures are thus generally between about −30° and +100° C., preferably between about −20° and +50° C., in particular between about −10 and +30° C.

The process is normally carried out under atmospheric pressure.

The reaction time can vary within wide limits; it is generally between about 0.5 and 12 hours.

The process according to the invention is for example carried out as follows. The inorganic base, at room temperature or below in the inert organic solvent, has added to it, with thorough mixing, first the amidosulfofluoride and then the diketene in such a way that the reaction temperature can be maintained at the desired level. The reaction mixture is subsequently stirred, with or without raising the temperature, until the characteristic IR bands of the diketene at 5.2 and 5.3$\mu$ are no longer detectable in the reaction product. The resulting salts of acetoacetamide-N-sulfofluoride with the inorganic base used are obtained in the form of colorless crystalline products.

The reaction products are characterized for example by (a) IR spectra which are compared with spectra of authentic material (prepared from acetoacetamide-N-sulfofluoride and the corresponding inorganic base), and (b) converting the products into the sweetener Acesulfame by means of 1 mol of methanolic KOH.

The latter reaction is the preferred way of determining the yield.

If desired, it is of course also possible to convert the salts which are obtained in the process into free acetoacetamide-N-sulfofluoride in conventional manner, for example by acidifying the salts with cold hydrochloric acid and isolating the resulting acetoacetamide-N-sulfofluoride by extraction, for example with ethyl acetate.

The following examples are intended to illustrate the invention in more detail.

EXAMPLE 1

76 g (0.55 mol) of potassium carbonate powder were presented at 0° C. in 500 ml of acetone. After addition of 57.8 ml (1 mol) of amidosulfofluoride, 84.3 ml (1.1 mol) of diketene were added dropwise in the course of 15 minutes. The mixture was then stirred at 0° C. for 30 minutes; the temperature was then allowed to rise to a maximum of 30° C. After about 30 minutes the exothermic reaction had ended, followed after a further 60 minutes by the end of $CO_2$ evolution (absence in IR spectra of the characteristic bands of diketene at 5.2 and 5.3$\mu$). The resulting potassium salt of acetoacetamide-N-sulfofluoride was obtained in the form of a colorless crystalline powder, was filtered off with suction and was washed with a little acetone. It was in all properties identical to authentic material prepared from acetoacetamide-N-sulfofluoride and potassium carbonate.

To determine the yield, the resulting potassium salt of acetoacetamide-N-sulfofluoride was suspended in 1 equivalent of 4 M to 6 M methanolic KOH solution and was converted in this form into the sweetener potassium salt of 6-methyl-3,4-dihydro-1,2,3-oxathiazin-4-one-2,2-dioxide.

The yield was 93% (of theory).

EXAMPLE 2

110.1 g (1.1 mol) of potassium hydrogencarbonate powder were presented at 0° C. in 500 ml of acetonitrile After addition of 57.8 ml (1 mol) of amidosulfofluoride, 84.3 ml (1.1 mol) of diketene were added dropwise in the course of 15 minutes. The subsequent course of the reaction, working up and determination of yield were carried out analogously to Example 1.

Yield 89% (of theory).

EXAMPLE 3

76 g (0.55 mol) of potassium carbonate powder were presented at 0° C. in 300 ml of dimethylformamide. After addition of 57.8 ml (1 mol) of amidosulfofluoride, 84.3 ml (1.1 mol) of diketene were added dropwise in the course of 15 minutes.

The mixture was then stirred at 0° C. for 30 minutes and then at a maximum of 30° C. for 90 minutes. After addition of 500 ml of acetone the potassium salt of acetoacetamide-N-sulfofluoride was filtered off with suction and washed with a little acetone. The characterization and yield determination were carried out as in Example 1.

Yield 90% (of theory).

EXAMPLE 4

58.3 g (0.55 mol) of sodium carbonate powder were presented at 0° C. in 500 ml of acetone. After addition of 57.8 ml (1 mol) of amidosulfofluoride, 84.3 ml (1.1 mol) of diketene were added dropwise in the course of 15 minutes. The mixture was then stirred at 0° C. for 30 minutes and then at a maximum temperature of 30° C. for 90 minutes. After addition of 500 ml of diethyl ether the sodium salt of acetoacetamide-N-sulfofluoride was filtered off with suction. Conversion with 1 equivalent of 4 M to 6 M methanolic KOH solution gave the potassium salt of the sweetener, which contained small amounts of the sodium salt of the sweetener. For that reason, the yield was determined by dissolving the salt mixture in a little water, bringing the solution to pH 1 with concentrated hydrochloric acid, and extracting the sweetener acid 6-methyl-3,4-dihydro-1,2,3-oxathiazin-4-one-2,2-dioxide with ethyl acetate.

Yield 84%.

EXAMPLE 5

40.6 g (0.55 mol) of lithium carbonate powder were presented at 0° C. in 500 ml of acetone. After addition of 57.8 ml (1 mol) of amidosulfofluoride, 84.3 ml (1.1 mol) of diketene were added dropwise in the course of 15 minutes. The subsequent course of reaction, working up and the yield determination were carried out analogously to Example 4.

Yield 86% (of theory).

We claim:

1. A process for preparing crystalline salts of acetoacetamide-N-sulfofluoride by reacting amidosulfofluoride $H_2NSO_2F$ with diketene in the presence of bases in an inert organic solvent, wherein the bases used are inorganic bases.

2. The process as claimed in claim 1, wherein the inorganic bases used are alkali metal carbonates and/or hydrogen carbonates, in particular potassium carbonate.

3. The process as claimed in claim 1, wherein the inorganic bases are used in an amount of at least 1 gram equivalent, preferably an excess up to about 20%, in particular only up to about 10%, based on one mol of amidosulfofluoride.

4. The process as claimed in claim 1, wherein the diketene is used in an at least substantially equimolar amount, preferably in an excess of up to about 30 mol %, in particular an excess between about 10 and 20 mol %, based on the amidosulfofluoride.

5. The process as claimed in claim 1, wherein the inert organic solvents used are aliphatic ketones, ethers, nitriles, carboxamides, sulfoxides and/or sulfones.

6. The process as claimed in claim 1, wherein the inert organic solvents used are acetone, acetonitrile and/or dimethylformamide, in particular acetone.

7. The process as claimed in claim 1, wherein the reaction is carried out at temperatures between about −30° and +100° C., preferably between about −20° and 50° C., in particular between about −10° and +30° C.

* * * * *